(12) United States Patent
Goodin

(10) Patent No.: US 6,193,685 B1
(45) Date of Patent: *Feb. 27, 2001

(54) PERFUSION CATHETER

(75) Inventor: Richard L. Goodin, Blaine, MN (US)

(73) Assignee: Schneider (USA) Inc., Minneapolis, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/756,044

(22) Filed: Nov. 26, 1996

(51) Int. Cl.[7] ................................................ A61M 29/00
(52) U.S. Cl. ................................ 604/102.01; 604/96.01; 604/523; 604/915
(58) Field of Search ............................... 604/96, 102, 101, 604/280, 96.01, 102.01, 102.02, 102.03, 523, 917, 915; 606/192, 194

(56) References Cited

U.S. PATENT DOCUMENTS

| 5,201,723 | | 4/1993 | Quinn . | |
|---|---|---|---|---|
| 5,219,335 | * | 6/1993 | Willard et al. | 604/164 |
| 5,295,961 | * | 3/1994 | Niederhauser et al. | 604/96 |
| 5,308,356 | * | 5/1994 | Blackshear, Jr. et al. | 606/194 |
| 5,334,154 | * | 8/1994 | Samson et al. | 604/102 |
| 5,415,636 | * | 5/1995 | Forman | 604/101 |
| 5,522,800 | * | 6/1996 | Crocker | 604/96 |
| 5,817,057 | * | 10/1998 | Berenstein et al. | 604/95 |
| 6,059,760 | * | 5/2000 | Sandmore et al. | 604/264 |

* cited by examiner

Primary Examiner—Sharon Kennedy
Assistant Examiner—Cris L. Rodriguez
(74) Attorney, Agent, or Firm—Westman, Champlin & Kelly, P.A.

(57) ABSTRACT

An improved perfusion system for a dilatation catheter includes inlet openings disposed at an acute angle with the normal direction of vascular flow.

8 Claims, 5 Drawing Sheets

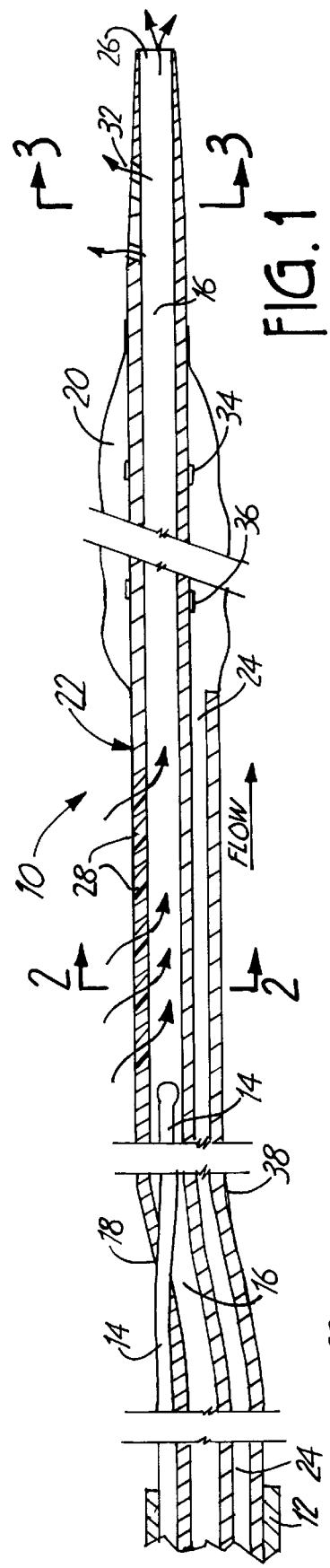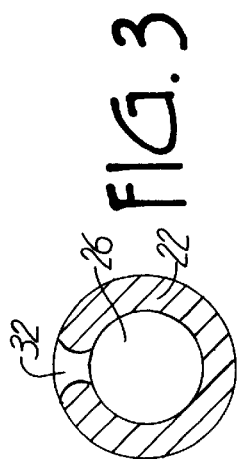

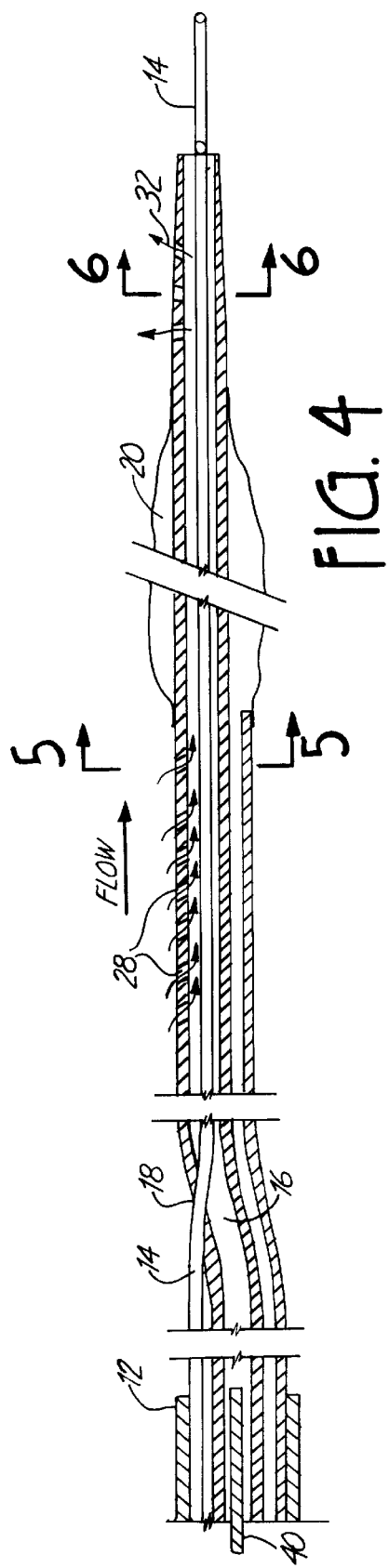
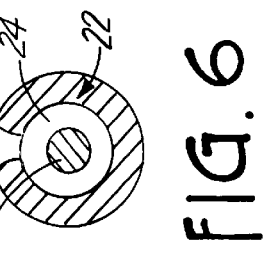
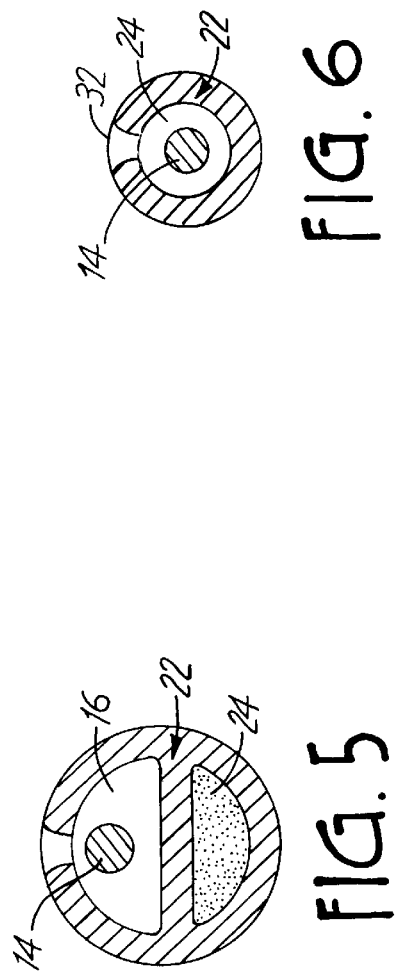

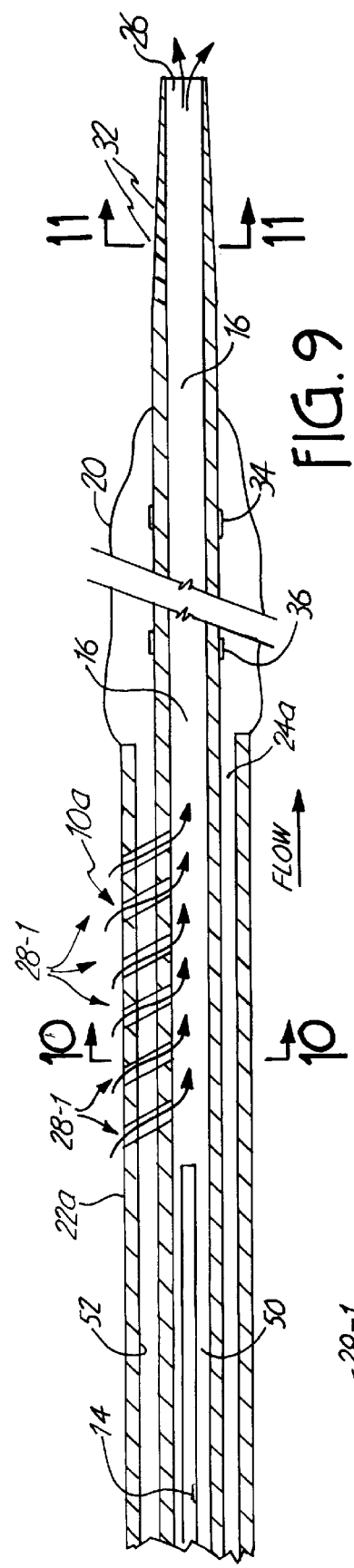

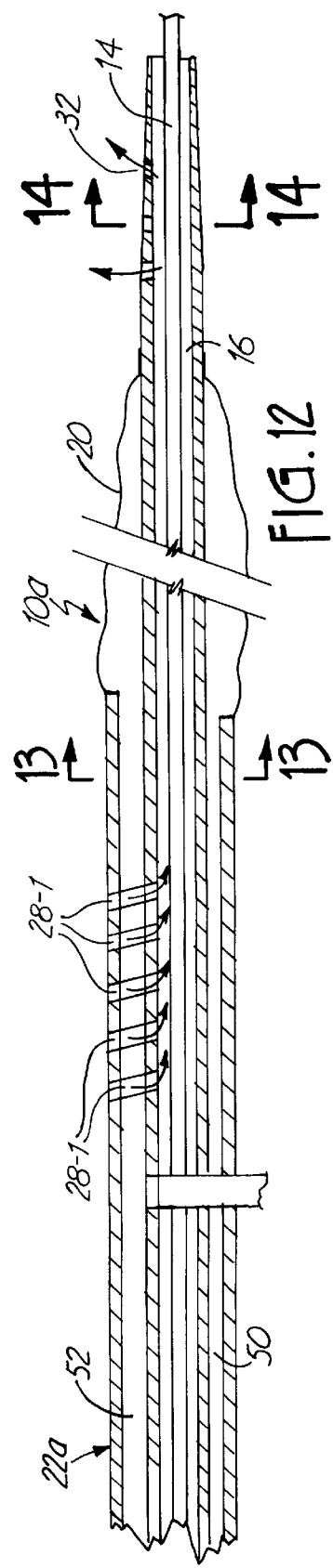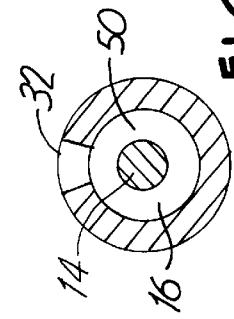
FIG.14
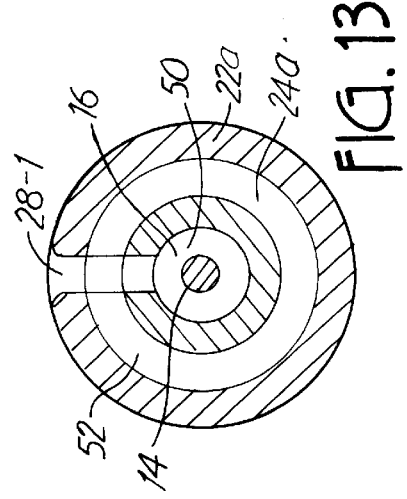
FIG.13
FIG.12

PERFUSION CATHETER

BACKGROUND OF THE INVENTION

I. Field of the Invention

The present invention is directed generally to catheter systems utilizing inflatable balloon dilatation devices for mechanical dilation of vascular stenoses and, more particularly, the invention addresses improvements in such systems related to the perfusion or bypassing of vessel fluid during such procedures to overcome limitations associated with the disruption of blood supply beyond the ditilation device that accompanies balloon expansion. Specifically, the invention deals with improvements in side opening flow passage arrangements including openings distal and proximal of the balloon in fluid communication with one another via a continuous lumen extending through and beyond the balloon.

II. Related Art

Percutaneous dilatation of arterial stenoses, particularly coronary artery stenoses, using a balloon dilatation catheter has become a recognized and common procedure that has proved to be effective in many instances. Inflation of the balloon to depress stenoses results in the obstruction of blood flow through the vascular passage of interest during the inflation. This, of course, is undesirable from the standpoint of loss of blood supply delivered to downstream tissues thus deprived. To prevent damage to these tissues, the inflation period of the balloon is limited to the time frame of about 2–3 minutes, after which the balloon must be deflated and flow allowed to pass to avoid tissue damage or even necrosis.

The dilatation time can be significantly lengthened, however, without increased risk of ischaemia by the provision of a bypass or perfusion system in which a passage is provided through the inflated balloon that enables vessel fluid flow to continue uninterrupted during the inflation or dilatation period.

Systems have been devised which include the provision of a perfusion path in dilatation catheters. One such system is illustrated and described in U.S. Pat. No. 5,201,723 to Quinn which incorporates a pattern of opposed elongated holes inclined and arranged to prevent kinking of the catheter. Another system is shown in U.S. Pat. No. 5,295,961 to Niederhauser et al that includes side openings connecting the vascular lumen with a common interior catheter lumen. The openings are arranged both distal and proximal of the balloon and the common catheter lumen extends through and beyond the balloon and are substantially perpendicular or normal to the longitudinal axis of the catheter in both the proximal and distal locations. The contents of U.S. Pat. No. 5,295,961 are deemed incorporated herein by reference for any purpose. While that system has accomplished perfusion and has met with a great deal of success, it would be more advantageous to provide a system that enjoys reduced pressure drop across the balloon system and reduces any tendency toward turbulent flow. In addition, severe directional changes and relatively sharp inlet and outlet opening edges may result in injury to blood cells as they negotiate the perfusion flow system. In this regard, it would be advantageous to provide an improved perfusion flow system in a dilatation catheter system which not only reduces pressure loss across the dilatation catheter and reduces the tendency toward turbulent flow, but which also provides a safer ingress and egress for the blood cells negotiating the system.

Accordingly, it is a primary object of the present invention to provide a perfusion flow system for a dilatation catheter which reduces the pressure drop across the balloon catheter and also reduces the tendency toward turbulent flow.

A further object of the present invention is to provide a perfusion flow arrangement for a dilatation catheter that reduces the tendency for blood cells negotiating the system to be damaged.

A still further object of the present invention is to provide a perfusion flow system for a dilatation catheter that maintains a blood flow of at least 40 cc/min. at about 80 mm Hg proximal perfusion pressure.

Other objects and advantages of the invention will occur to those skilled in the art upon familiarization with the description and accounts contained in the specification, together with the appended claims.

SUMMARY OF THE INVENTION

The present invention provides improvements in perfusion flow systems for vascular dilatation catheter devices which utilize an expanding member to provide mechanical dilation of coronary or other arterial stenoses in a procedure which temporarily blocks the vessel. The improvements of the invention modify the perfusion path and reduce the tendency toward turbulent flow and reduce pressure losses, but not the flow across the dilatation catheter. At the same time, the invention also provides a safer passage for blood cells navigating or flowing through the perfusion system. The system is designed for use with a typical balloon dilatation catheter system which utilizes a bilumen tubular member or shaft carrying an expandable balloon member and designed with two elongate, parallel lumens, one of which is in fluid communication with the balloon cavity and with an external source of inflation fluid for selectively inflating and deflating the expansible balloon member (nominally called herein the inflation lumen) and the other one of which traverses the expansible member or dilatation device and is nominally utilized for carrying a guidewire (called herein the guidewire lumen or the perfusion lumen), but which also provides the passage for the perfusion flow.

In accordance with one aspect of the invention, a pattern of perfusion openings or passages are provided in the bilumen tubular catheter member which provide inlet and outlet passages between and connecting the outside of the tubular member with the perfusion lumen proximal and distal the dilatation device which, with an intervening common segment of the lumen, provide a passage for blood or other fluid through the expansible dilatation member to supply points downstream in the normal direction of flow during balloon expansion.

In accordance with one aspect of the invention, the openings or passages proximal to the dilatation device are designed to breach the catheter wall at an acute angle with the normal axis or center line of the tubular catheter member (and thus with the vascular lumen) so as to reduce or minimize the deflection angle from the normal path between the local vascular blood flow and the by-pass or perfusion lumen. In addition to the angled posture of the openings, the outer edges that impinge entering blood cells are preferably flared to present a blunt edge to reduce cell injury and reduce tendencies toward turbulence in the flow pattern. The distal openings may also be designed to exit through the wall of the bilumen tubular member at an acute angle with the direction of flow if desired, however, the distal end of the guidewire lumen is typically open to accommodate a guidewire extending beyond the distal end thereof and this provides a main perfusion outlet channel parallel to the flow direction.

It has been found that it is preferable to locate the openings close to the dilatation device or balloon. The pattern of the openings may be linear, but any desired pattern can be used. The desired flow rate to be maintained in a coronary artery, for example, is approximately 40 cc/min at 80 mm Hg upstream or proximal perfusion pressure. For a lumen typically 0.031 in. (0.079 cm) to 0.036 in. (0.091 cm) I.D., the number of perfusion inlet openings required may range from about 25 openings having a nominal diameter of 0.14 in. (0.036 cm) to about 10 openings having a nominal diameter of 0.025 in. (0.064 cm). The distal guidewire opening in the guidewire perfusion lumen is about 0.018 in. (0.046 cm) for a guidewire having a diameter of 0.014 in. (0.036 cm). A lesser number of distal side openings are also provided, but, preferably, the flow area at the outlet is greater than that at the inlet and both inlet and outlet openings are designed so that the flow is limited only by the diameter (capacity) of the guidewire or perfusion lumen itself.

In operating the system, a guide catheter is introduced arterially and advanced subcutaneously through the vascular system to a point close to the stenoses of interest. Whereupon, the quidewire is typically introduced and extended beyond the distal end of the catheter to initially breach the stenoses and thereafter position the expandable balloon member adjacent the stenoses in the collapsed state for the procedure. Once the device is positioned in the vessel, the guidewire is retracted beyond the dilatation device and proximal perfusion openings to thereby fully open the perfusion route to flow.

It has been found that the angle of incidence for the inlet openings proximal the expanding dilatation device is ideally between about 30° and 70° and typically a 45° angle is preferred. Whereas the distal openings can also be angled, it is less important that this be the case.

It should be noted that the invention is applicable to any type of catheter of the class utilized for dilatation, including those made of polyalkane material, such as polyethylene, polyester material, such as hytril, polyethylene terphthlate (PET), polyamides, including various nylons, combinations of these and other materials commonly utilized in such devices. The holes may be formed utilizing a hollow needle punch, for example, a $CO_2$ laser drill, or any other suitable method of comparable precision.

The perfusion system of the present invention should normally allow a dilatation device to remain inflated in a coronary artery safely for up to 15 minutes compared to the 2–3 minutes presently allowable without perfusion. It is also anticipated that vascular flow in the reverse direction from that illustrated herein would readily be accommodated. It also is anticipated that the guidewire lumen can also be used for the infusion of flushing fluid as to alleviate any clogging of the system, or the like.

BRIEF DESCRIPTION OF THE DRAWINGS

In the drawings wherein like numerals are utilized to designate like parts throughout the same:

FIG. 1 depicts a cross sectional compressed view, with parts broken, through a distal area of a catheter system including the invention and showing the controllable guidewire drawn partially back for the purpose of allowing free perfusion;

FIG. 2 is a cross sectional view taken substantially along line 2—2 of FIG. 1;

FIG. 3 is a cross sectional view taken substantially along line 3—3 of FIG. 1;

FIG. 4 depicts a view of a distal section of a catheter system similar to FIG. 1, but in which the controllable guidewire is extended to protrude slightly beyond the distal opening of the catheter;

FIG. 5 is a cross sectional view taken substantially along line 5—5 of FIG. 4;

FIG. 6 is a cross sectional view taken substantially along line 6—6 of FIG. 4;

FIGS. 9–14 illustrate an alternate embodiment perfusion system for a coaxial catheter system.

DETAILED DESCRIPTION

Figure 7:
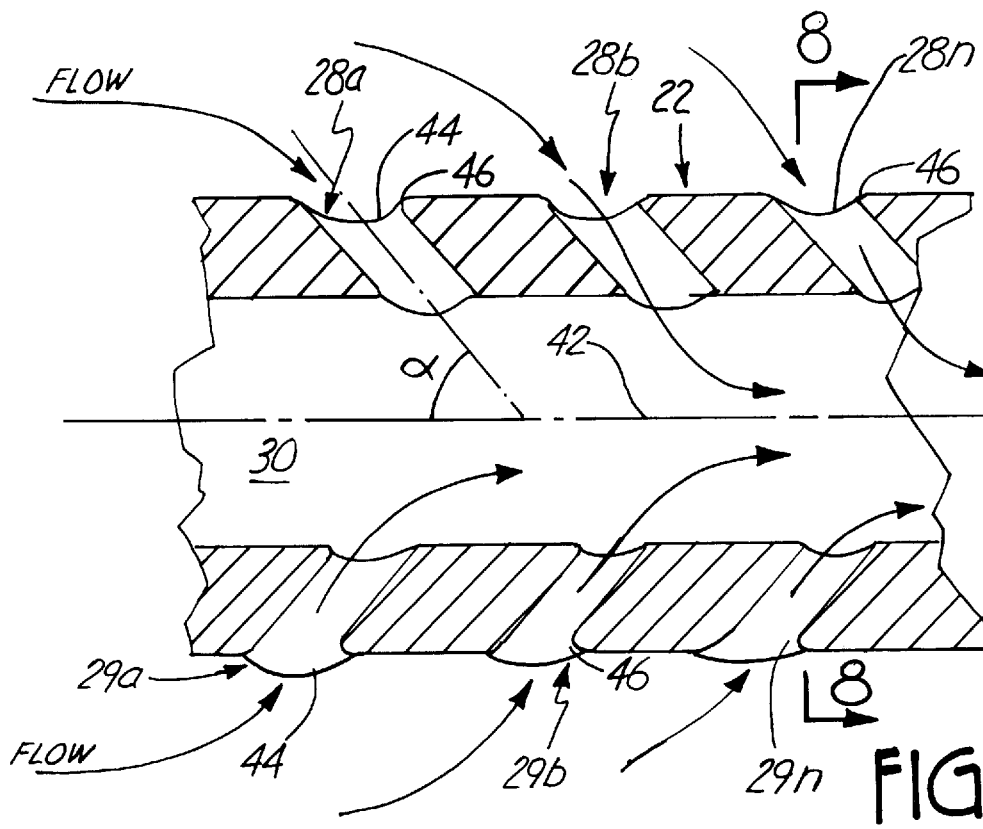
FIG. 7 is a greatly enlarged fragmentary view of the guidewire or perfusion lumen depicting perfusion openings therein in relation to fluid flow.

The perfusion system in accordance with the invention as illustrated by the drawing figures generally is applied to a bilumenal catheter tube of side-by-side configuration. This is meant to be illustrative only and by no means limiting as coaxial systems, for example, or many other systems of catheter lumen combinations that carry blocking devices benefit equally from the concepts as well.

FIGS. 1 and 4 depict cross sectional views with parts broken away through a distal portion of a catheter system including a dilatation system provided with the perfusion system of the invention generally denoted by 10 and showing the dilatation catheter system emerging from the distal end of a guide catheter 12 including a guidewire 14 which emerges from the guide catheter 12 and enters guidewire lumen 16 at 18. The dilatation balloon 20 is connected in a well-known manner to the two-lumen dilatation shaft 22 of the balloon dilatation catheter and is supplied with inflating fluid through a second elongated inflation lumen 24 which connects the balloon with a source of inflation fluid supplied at the proximal end of the catheter system in a well-known manner (not shown). As can be seen from FIGS. 1 and 4, the guidewire lumen 16 (also for the purposes of this description the perfusion lumen) extends through and beyond the balloon shown inflated at 20 to an open end at 26. A series of angled inlet opening passages 28 (see also FIG. 7) are provided proximal to balloon 20 and extend through the sidewall 30 of the catheter shaft 22 at an acute angle α with the indicated direction of flow. Additional outlet perfusion openings 32 are provided distal the balloon 20 and these together with the bore opening 26 and the common lumen segment provide an uninterrupted path of flow through the balloon 20 whether or not the balloon is inflated.

In FIG. 1, the guidewire 14 is shown retracted beyond the proximal openings 28 so that the guidewire does not interfere in any manner with the perfusion flow path in the lumen segment 30. In FIG. 4, guidewire 14 is illustrated as being fully extended through the balloon 20 in its leading or navigating position. The guidewire is typically extended to lead the dilatation shaft 22 of the catheter through the stenoses sight of interest, to initially breach the stenoses with the balloon system following thereafter to be located as desired for the dilatation procedure. Once the device is positioned in the vessel, the guidewire is retracted as shown in FIG. 1 beyond the dilatation device and proximal perfusion holes to thereby fully open the perfusion route to flow. Radiopaque markings can be utilized to locate the proper position for the tip of the guidewire to occupy when retracted so that it is not withdrawn beyond the opening at 18 in the lumen 16 and remains threaded in the catheter.

Likewise, marking rings can be utilized at the dilatation balloon itself to aid in properly positioning that device adjacent the stenoses of interest. These are illustrated at 34 and 36 with respect to the balloon and at 38 with respect to the catheter shaft.

As shown in FIG. 4, a temporary strengthening wire 40 may be provided to assist in the vascular navigation of the catheter system. Such a wire may be provided with a surface of reduced friction material such as polytetrafluoroethylene (PTFE), certain nylons and other low friction materials for easy insertion and retraction. The nominal external diameter of the shaft 22 is generally about 0.10 cm in the vicinity just proximal the balloon member 18 and somewhat less, possibly about 0.08 cm proximal the outlet opening 26. The catheter shaft 22 may be comparatively soft without the strengthening wire 40 in some embodiments and great care must be taken in its manipulation through the arterial vascular system. Other configurations such as coaxial arrangements are typically more rigid.

With respect to the passages 28 and 32, it has been found that it is preferable to locate the openings close to the dilatation device or balloon 18. The pattern of openings may be linear, as illustrated, but any other desired pattern can be employed.

Figure 8:
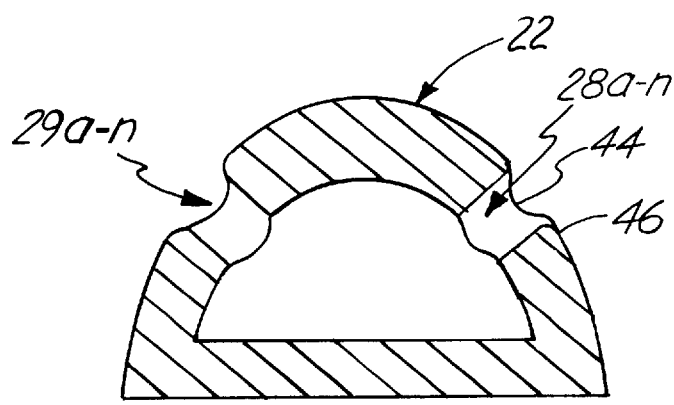
FIG. 8 is a cross sectional view taken substantially along line 8—8 of FIG. 7.

As shown particularly in FIGS. 7 and 8, it will be appreciated that the passages as at 28 achieve an acute angle with the catheter axis and so the axis of flow along the vascular passage of interest as illustrated at 42. This angle a is preferably from about 30° to about 70° and most preferably about 45°. It should further be noted that the outer openings 44 of the passages 28 are preferably contoured or flared as at 46 to further blunt the edges with respect to the blood cells entering the lumen 30 through the passages 28. In addition, this aids in maintaining a laminar flow pattern within the lumen segment which thereby also reduces damage to the blood cells utilizing the passage while maintaining a maximum flow rate through the passage.

The desired flow rate to be maintained in a coronary artery, for example, is approximately 40 cc/mm at 80 mm Hg. For a lumen 0.031 in. (0.079 cm) to 0.036 in. (0.091 cm) I.D., the number of perfusion inlet openings required may range from about 25 openings having a nominal diameter of 0.14 in. (0.036 cm) to about 10 openings having a nominal diameter of 0.025 in. (0.064 cm). The distal guidewire opening 26 in the guidewire perfusion lumen 16 is about 0.018 in. (0.046 cm) for a guidewire having a diameter of 0.014 in. (0.036 cm). A lesser number of the distal side openings 32 are provided, but, preferably, the flow area at the outlet is greater than that at the inlet and both inlet and outlet openings are designed so that the flow is limited only by the diameter (capacity) of the guidewire or perfusion lumen itself.

It should be noted that the invention is applicable to any type of catheter of the class utilized for dilatation, including those made of polyalkane material, such as polyethylene, polyester material, such as hytril, polyethylene terphthlate (PET), polyamides, including various nylons, combinations of these and other materials commonly utilized in such devices. The holes may be formed utilizing a hollow needle punch, for example, a $CO_2$ laser drill, or any other suitable method of comparable precision.

In operation, for dilatation of an identified stenoses, the guide catheter 12 is introduced via the arterial system, typically through the femoral artery in the leg, and advanced percutaneously to a point at or close to the stenoses of interest. The guidewire 14 is then advanced beyond the dilatation device 20 through the lumen 16 and opening 26, as shown in FIG. 4, traversing the stenoses until its distal end lies distal of the stenoses. The guidewire, while easily deflected, as is the case with the stiffener 40, has a surface provided with a very low friction co-efficient and so it can readily be advanced and controlled in a virtually unimpeded fashion. This having been accomplished, dilatation catheter shaft 22 can be advanced along the guidewire 14 until the dilatation balloon 20 is positioned in the stenoses. The balloon 20 can then be dilated in a known manner utilizing fluid supply along the lumen 24 and the guidewire 14 retracted to a position such as shown in FIG. 1. In this manner, perfusion is not impeded by either the expanded balloon or the presence of the guidewire in the common lumen segment. Thus, the balloon may remain inflated for an extended period of time and thereby provide improved results with regard to expansion of the stenoses.

FIGS 9–14 are similar to FIGS. 1–6 and illustrate an embodiment of a perfusion system for a coaxial catheter system 10a, where like numbers are used to refer to like parts in FIGS. 1–6. The catheter includes coaxial inner and outer lumens 50, 52. Inner lumen 50 forms a guide wire lumen and outer lumen 52 forms an inflation lumen as is generally known. As with previous embodiments, inner lumen 50 or guide wire lumen forms the perfusion lumen which extends through and beyond the balloon 20. Similarly, catheter 10a includes inlet passages 28–1 proximal the balloon which extend through the sidewall of the catheter shaft 22a at an acute angle α with the indicated direction of flow to the inner or perfusion lumen 50 and outlet perfusion openings 32 distal of the balloon 20 opened to inner lumen 50 or perfusion lumen to provide an uninterrupted path of flow through the balloon whether or not the balloon is inflated. In FIG. 9, guide wire 14 is retracted so that the guide wire 14 does not interfere with the perfusion flow path and in FIG. 12, guidewire 14 is fully extended in its leading or navigating position as previously explained for FIGS. 1–6.

This invention has been described herein in considerable detail in order to comply with the patent statutes and to provide those skilled in the art with the information needed to apply the novel principles and to construct and use embodiments of the example as required. However, it is to be understood that the invention can be carried out by specifically different devices and that various modifications can be accomplished without departing from the scope of the invention itself.

What is claimed is:

1. A balloon dilatation perfusion catheter, comprising:

(a) a balloon defining a cavity therein;

(b) an elongate tubular catheter member for navigating a vascular passage of interest and carrying said balloon, said catheter member having a distal end extending through and beyond the balloon and a proximal end;

(c) a first lumen in said tubular catheter member in fluid communication with said balloon cavity and with a source of inflation fluid for selectively inflating and deflating said balloon;

(d) a second lumen in said tubular member extending therealong from a point proximal said balloon through and beyond said balloon and having a distal end opening distal of said balloon, said second lumen being designed to accommodate a guide wire therein;

(e) a plurality of perfusion openings for permitting vascular fluid to by-pass said balloon including inlet perfusion openings in said tubular catheter member connecting to said second lumen arranged proximal said balloon, said inlet perfusion openings having passages sloped from a mouth of the passage inwardly toward the second lumen at an acute angle of between about 30° and 70° relative to and in a direction of fluid toward the passage and a plurality of outlet perfusion openings in said tubular catheter member connecting with said second lumen and having passages sloped from a mouth of the passage outwardly from the second lumen at an acute angle relative to and in the direction of fluid flow toward the passage;

(f) wherein said plurality of perfusion openings include openings arranged in a pattern comprising a plurality of spaced openings;

(g) wherein said inlet and outlet perfusion openings are non-protruding with respect to said second lumen and provide with a connecting segment of said second lumen, a continuous and unobstructed perfusion flow passage notwithstanding said balloon; and (h) wherein said tubular catheter member has an outer surface and wherein said inlet perfusion openings are flared proximate said outer surface of said tubular catheter member to present blunt entry surfaces to blood cells negotiating said openings to reduce cell damage.

2. The apparatus of claim 1 wherein said perfusion openings have a diameter range from about 0.015 in. (0.038 cm) to about 0.025 in. (0.064 cm), and the aggregate area of the inlet perfusion openings and outlet perfusion openings is such that it enables the passage of a minimum amount of blood flow of 40 cc/min. at a pressure differential of 80 mm Hg proximal perfusion pressure and in the absence of a guide wire.

3. The apparatus of claim 2 wherein said tubular catheter member is a bilumenal member selected from the group consisting of side-by-side and coaxial lumen configurations.

4. The apparatus of claim 3 wherein said acute angle is 45°.

5. The apparatus of claim 1 wherein said tubular catheter member is a bilumenal member selected from the group consisting of side-by-side and coaxial lumen configurations.

6. The apparatus of claim 1 wherein said acute angle is 45°.

7. The apparatus of claim 1 wherein both said plurality inlet perfusion openings and plurality outlet perfusion openings are flared proximate the outer surface.

8. A balloon dilatation perfusion catheter, comprising:

(a) a balloon defining a cavity therein;

(b) an elongate tubular catheter member for navigating a vascular passage of interest and carrying said balloon, said catheter member having a distal end extending through and beyond the balloon and a proximal end;

(c) a first lumen in said tubular catheter member in fluid communication with said balloon cavity and with a source of inflation fluid for selectively inflating and deflating said balloon;

(d) a second lumen in said tubular member extending therealong from a point proximal said balloon through and beyond said balloon and having a distal end opening distal of said balloon, said second lumen being designed to accommodate a guide wire therein;

(e) a plurality of perfusion openings for permitting vascular fluid to by-pass said balloon including proximal perfusion openings in said tubular catheter member connecting to said second lumen arranged proximal said balloon, said proximal perfusion openings having passages sloped at an acute angle of between about 30° and 70° relative to and in the direction of fluid toward the passage and a plurality of distal perfusion openings in said tubular catheter member connecting with said second lumen and having passages sloped at an acute angle relative to and in the direction of fluid flow toward the passage;

(f) wherein said plurality of perfusion openings include openings arranged in a pattern comprising a plurality of spaced openings; and (g) wherein said proximal and distal perfusion openings are non-protruding with respect to said second lumen and provide with a connecting segment of said second lumen, a continuous and unobstructed perfusion flow passage notwithstanding said balloon.

* * * * *